United States Patent
Melkent et al.

(10) Patent No.: US 7,615,077 B2
(45) Date of Patent: Nov. 10, 2009

(54) INTERVERTEBRAL IMPLANTS WITH RADIAL TEETH AND METHODS OF USE

(75) Inventors: Anthony J. Melkent, Memphis, TN (US); Lindsey Gardner Waugh, Memphis, TN (US)

(73) Assignee: Warsaw Orthopedic, Inc.

( * ) Notice: Subject to any disclaimer, the term of this patent is extended or adjusted under 35 U.S.C. 154(b) by 287 days.

(21) Appl. No.: 11/394,452

(22) Filed: Mar. 31, 2006

(65) Prior Publication Data
US 2007/0233263 A1    Oct. 4, 2007

(51) Int. Cl.
*A61F 2/44*    (2006.01)
(52) U.S. Cl. .................................... 623/17.11
(58) Field of Classification Search .......... 606/61, 606/60, 246–249; 623/17.11–17.16
See application file for complete search history.

(56) References Cited

U.S. PATENT DOCUMENTS

| | | | |
|---|---|---|---|
| 4,349,921 A | 9/1982 | Kuntz | |
| 4,834,757 A * | 5/1989 | Brantigan | 623/17.11 |
| 4,865,603 A | 9/1989 | Noiles | |
| 5,306,308 A * | 4/1994 | Gross et al. | 623/17.16 |
| 5,425,772 A * | 6/1995 | Brantigan | 623/17.11 |
| 5,658,335 A | 8/1997 | Allen | |
| 5,702,450 A | 12/1997 | Bisserie | |
| 6,143,033 A | 11/2000 | Paul et al. | |
| 6,346,122 B1 | 2/2002 | Picha et al. | |
| 6,416,551 B1 | 7/2002 | Keller | |
| 6,458,159 B1 * | 10/2002 | Thalgott | 623/17.11 |
| 6,558,424 B2 | 5/2003 | Thalgott | |
| 6,716,245 B2 * | 4/2004 | Pasquet et al. | 623/17.11 |
| 6,827,740 B1 | 12/2004 | Michelson | |
| 6,986,788 B2 * | 1/2006 | Paul et al. | 623/17.11 |
| 7,137,997 B2 * | 11/2006 | Paul | 623/17.11 |
| 2002/0087212 A1 * | 7/2002 | James et al. | 623/17.11 |
| 2002/0177898 A1 * | 11/2002 | Crozet | 623/17.11 |
| 2003/0181981 A1 * | 9/2003 | Lemaire | 623/17.11 |
| 2005/0143822 A1 | 6/2005 | Paul | |

\* cited by examiner

*Primary Examiner*—Thomas C Barrett
*Assistant Examiner*—Michael J Araj

(57) ABSTRACT

The present application is directed to intervertebral implants including teeth arranged in a radial pattern to resist expulsion in multiple directions. The teeth may include a variety of shapes and orientations. In one embodiment, the implant includes an annular shape with a central opening. The implant may further be tapered along a section or entirety of an insertion edge to distract the adjacent vertebral members upon insertion of the implant into the intervertebral space.

26 Claims, 5 Drawing Sheets

INTERVERTEBRAL IMPLANTS WITH RADIAL TEETH AND METHODS OF USE

BACKGROUND

The present application is directed to devices and methods for stabilizing vertebral members, and more particularly, to intervertebral implants with radial teeth for replacing an intervertebral disc, vertebral member, or combination of both to distract and/or stabilize the spine.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

Various procedures include replacing the entirety or a section of a vertebral member, the entirety or a section of an intervertebral disc, or both. One or more replacement implants may be inserted to replace the damaged vertebral members and/or discs. The implants reduce or eliminate the pain and neurological deficit, and increase the range of motion.

SUMMARY

The present application is directed to intervertebral implants. The implants may include inferior and superior surfaces that contact the adjacent vertebral members. Teeth are positioned on one or both of these surfaces to resist expulsion of the implant after insertion. The teeth may be arranged in a radial pattern to prevent expulsion in many directions. The radial pattern may be spread across the faces of the surfaces, or may be limited to a limited area. In one embodiment, the implant includes an annular shape having a central opening. The implant may also be wedge-shaped to distract the vertebral members during insertion.

DETAILED DESCRIPTION

The present application is directed to intervertebral implants including teeth arranged in a radial pattern to resist expulsion in multiple directions. In one embodiment, the implant includes an annular shape with a central opening. The implant may further be tapered along a section or entirety of an insertion edge to distract the adjacent vertebral members upon insertion of the implant into the intervertebral space.

Figure 1:
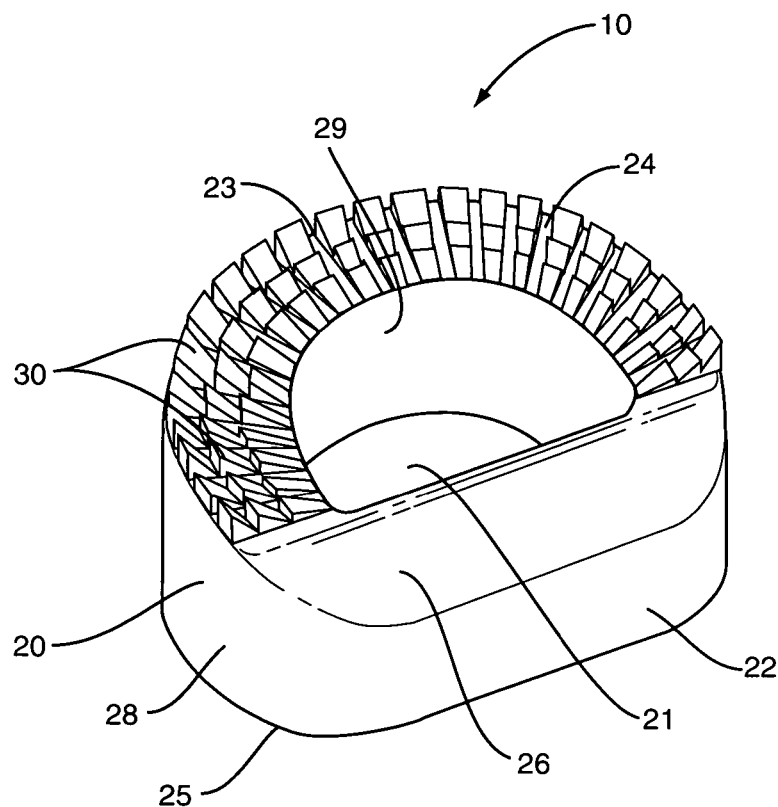
FIG. 1 is a perspective view illustrating an implant according to one embodiment.

FIG. 1 illustrates one embodiment of an implant 10. The implant 10 includes a body 20 sized to fit within the intervertebral space with a superior surface 24 and an inferior surface 25 that contact adjacent vertebral members. The superior and inferior surfaces 24, 25 may be substantially parallel, or may be non-parallel. In one embodiment, body 20 includes a substantially straight posterior edge 22 and an arcuate anterior edge 23. The shape of the body 20 may be configured to match the body or anterior arch of the vertebral members. Body 20 further includes an outer edge 28 and an inner edge 29.

Figure 2:
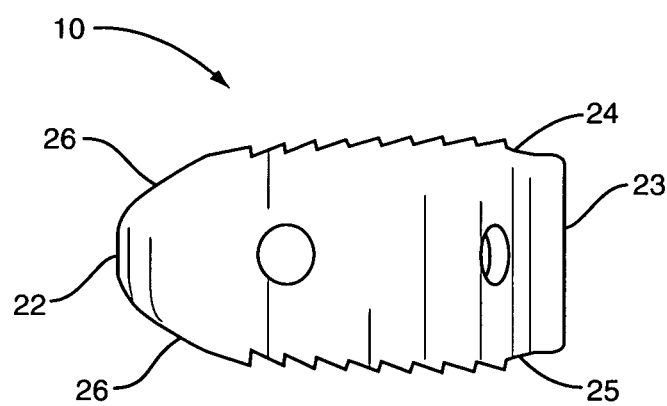
FIG. 2 is a side view illustrating an implant according to one embodiment.
Figure 3:
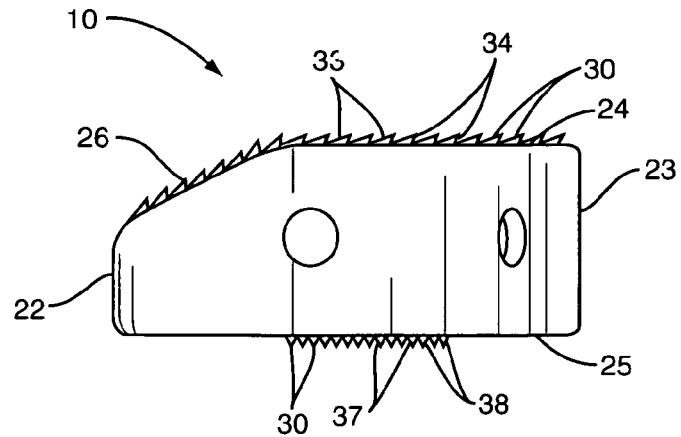
FIG. 3 is a side view illustrating an implant according to one embodiment.

FIG. 2 illustrates a side view of one embodiment of an implant 10 with a tapered section 26 at the posterior edge 22. The reduced height of the tapered section 26 facilitates insertion of the implant 10 between the vertebral members when inserted in an anterior approach. The tapered section 26 further distracts the vertebral members during insertion of the implant 10. The tapered section 26 may include a variety of different shapes and dimensions. In one embodiment as illustrated in FIG. 2, the superior and inferior surfaces 24, 25 of the tapered section 26 extend at substantially the same angle from the posterior edge 22. FIG. 3 illustrates an embodiment with a tapered superior surface 24 with the inferior surface 25 being substantially flat.

Figure 4:
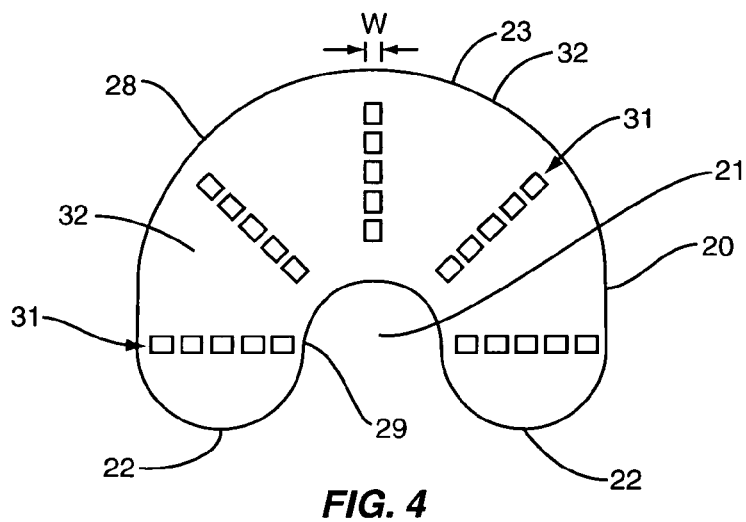
FIG. 4 is a top view illustrating an implant according to one embodiment.
Figure 5:
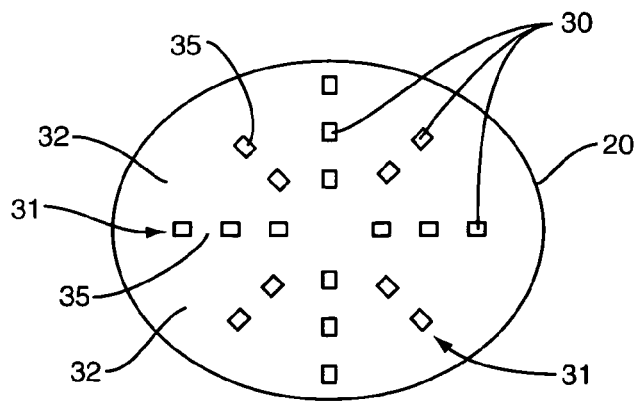
FIG. 5 is a top view illustrating an implant according to one embodiment.

In one embodiment as illustrated in FIG. 1, the body 20 includes an annular shape forming an opening 21 within a central region. The opening 21 may be completely contained within the body 20 as illustrated in FIG. 1, or the opening 21 may open to the exterior as illustrated in FIG. 4. In the embodiment of FIG. 4, the body 20 is substantially U-shaped and does not include an enclosed central area. With a U-shaped body 20, the legs may be aligned for the opening 21 to open in either the anterior, posterior, or lateral directions. FIG. 5 illustrates a body 20 with continuous superior and inferior surfaces 24, 25 with no opening 21. The body 20 of FIG. 5 is substantially oval in shape, although other shapes may also be included.

Teeth 30 are positioned on one or both of the superior and inferior surfaces 24, 25. Teeth 30 may extend across the entirety of the surfaces 24, 25, or across a limited section. In one embodiment, no teeth are positioned on the tapered section 26 to facilitate insertion of the device 10. In one embodiment, the tapered section 26 is substantially smooth.

Figure 6:
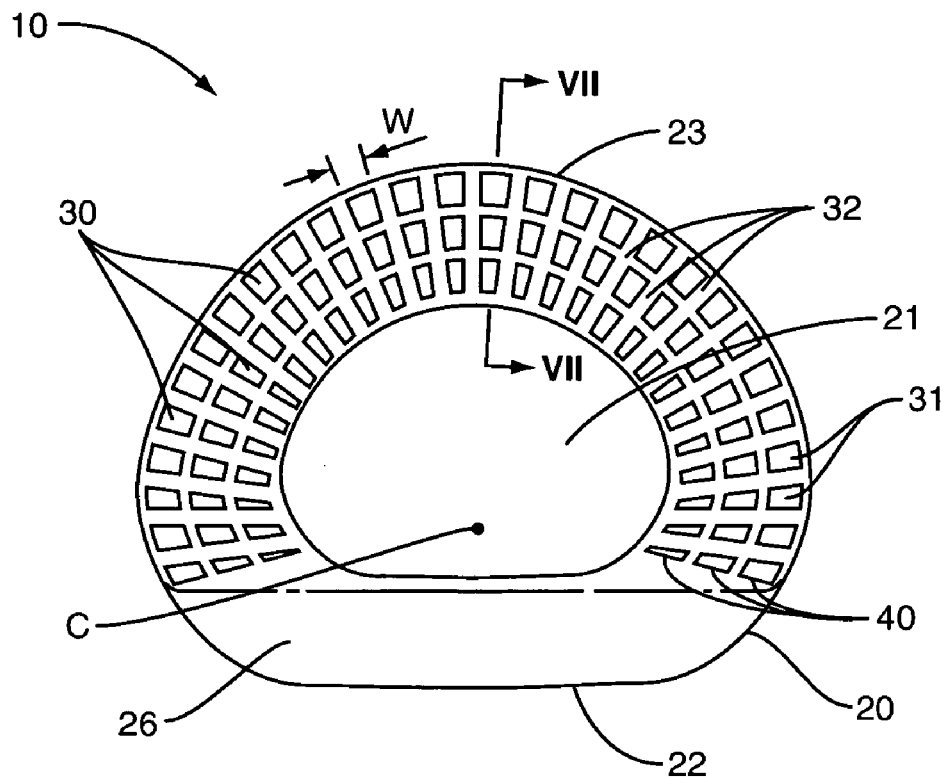
FIG. 6 is a top view illustrating an implant according to one embodiment.

FIG. 6 illustrates one embodiment of the teeth 30 aligned in a radial pattern along the surface of the body 20. This radial pattern forms a serration pattern that resists expulsion in multiple directions once the implant 10 is inserted within the intervertebral space. In this embodiment, the teeth 30 are aligned in substantially concentric ridges 40 and further formed into rows 31 that radially extend outward from a central point C of the body 20. Point C may be the actual center of the body 20, or may be positioned in proximity to the center. In one embodiment, radial aisles 32 are positioned between each of the teeth rows 31. The aisles may be smooth or may include a roughened surface. The aisles 32 may be used for applying a bone growth material to the implant prior to insertion. Aisles 32 may also gather bone and tissue fragments that are removed from the vertebral members during insertion of the implant.

In the embodiment of FIG. 6, the width w of the teeth 30 increases towards the outer edge 28 of the body 20. The teeth 30 in proximity to the opening 21 include a smaller width with the teeth 30 at the outer edge include a greater width. The increasing width of the teeth 30 results in a width of the aisles 32 being substantially the same between the inner and outer edge of the body 20.

Figure 7:
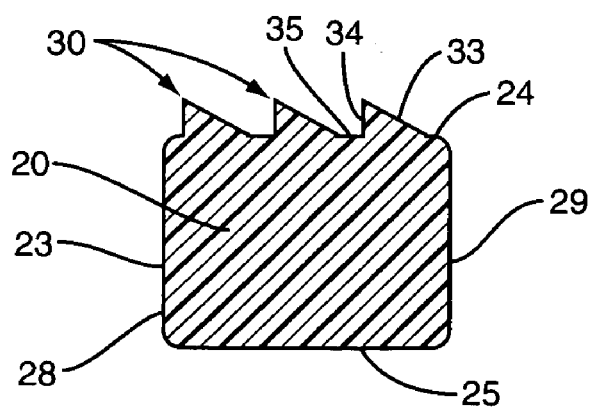
FIG. 7 is a cross-section view cut along line VII-VII of FIG. 6 illustrating an implant according to one embodiment.

FIG. 7 illustrates the configuration of the teeth 30 according to one embodiment. In this embodiment, the row 31 comprises three teeth 30. Each tooth 30 includes a first ramped surface 33 and a second surface 34. First and second surfaces 33, 34 may be positioned at a variety of angles. In one embodiment, the first surface 33 angles towards the outer edge of the body 20, and the second surface 34 is substantially parallel to the outer edge 28. This particular row 31 prevents expulsion of the device 10 in an anterior direction as the corner formed by the surfaces 33, 34 digs into the vertebral members during movement in an anterior direction. Space 35 is positioned between each of the teeth 30. The teeth 30 are distanced apart with a space 35 positioned between the first ramped surface 33 of a first tooth and the second surface 34 of an adjacent tooth. The space 35 may provide for receiving bone growth material or bone and tissue fragments caused during insertion of the implant.

Figure 10:
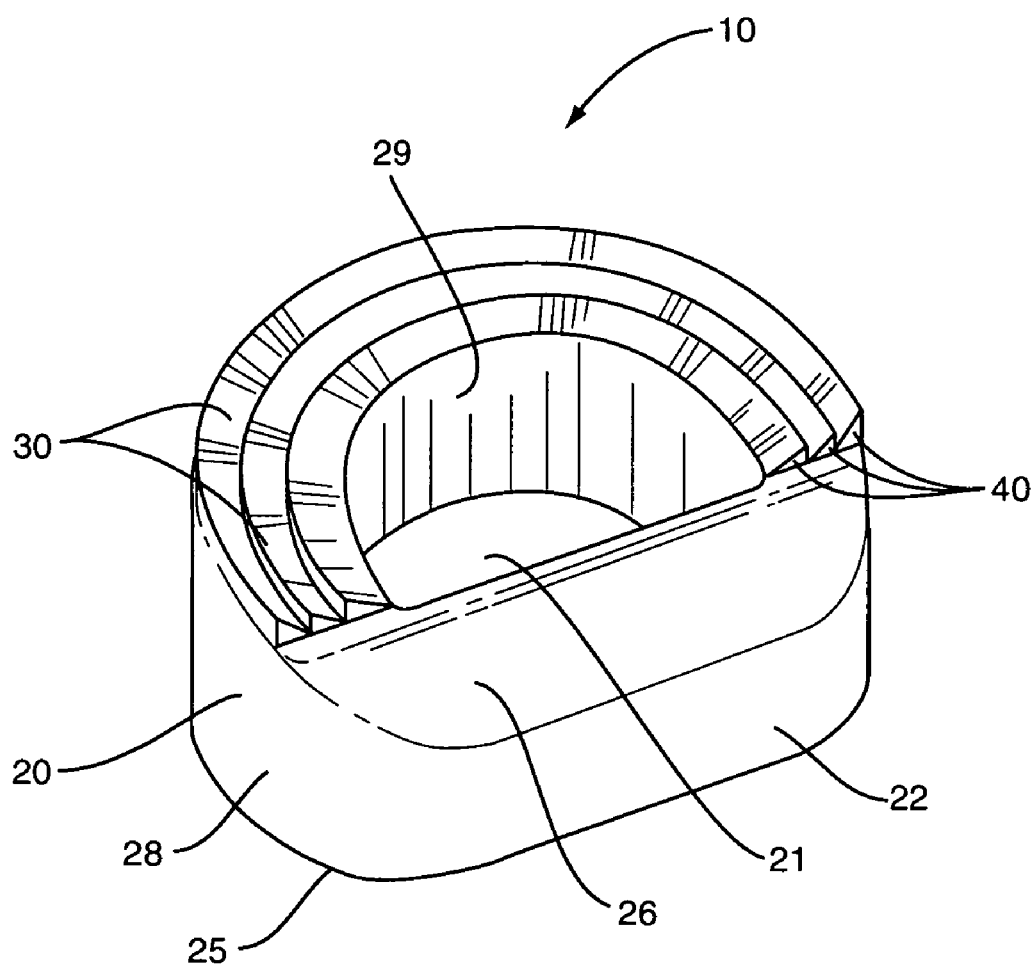
FIG. 10 is a perspective view illustrating an implant according to one embodiment.

FIG. 10 includes a plurality of substantially concentric ridges 40 that form rows 31 of teeth 30. In this embodiment, the continuous design of the ridges 40 eliminate the aisles 32 between rows 31, and still provide for a radial arrangement with the teeth 30 orientated towards the central opening 21. The ridges 40 extend continuously around a section of the body 20, such as the non-tapered section. The embodiment of FIG. 10 features 3 continuous ridges 40. In other embodiments, one or more of the ridges 40 may be divided into discrete sections.

FIG. 4 illustrates another pattern of teeth 30. In this embodiment, rows 31 are spread apart in intervals about the surface of the body 20. Each of the rows 31 is substantially straight and radially extends outward from a point oriented at or near the center of the body 20. The width w of the teeth 30 are substantially constant from the inner edge 29 to the outer edge 28 of the body 20. This shape results in the aisles 32 between the rows 31 increasing in width from the inner edge 29 to the outer edge 28.

FIG. 5 illustrates another embodiment with the teeth 30 being arranged in radial rows 31 that are staggered across the surface of the body 20. The rows 31 include two or three teeth with an enlarged space 35 positioned therebetween. The teeth 30 in adjacent rows 31 are staggered and approximately align with the space 35. Each of the teeth 30 across the surface is aligned in a radial pattern from a central point on the surface of the body 20. In this embodiment, aisles 32 are formed between each row 31 and include an enlarged width that increases towards the outer edge of the body 20.

Each of the teeth 30 may be substantially the same or may be different. FIG. 3 illustrates an embodiment with a first type of teeth 30 on the superior surface 24 and a second type of teeth 30 on the anterior surface 25. The superior teeth 30 include a first ramped surface 33 and a second surface 34 positioned at angles to resist expulsion in a particular direction. The spacing of the teeth 30 is tight such that the ramped surface 33 of a first tooth 30 leads directly into the second surface 34 of an adjacent tooth 30. The anterior teeth 30 are substantially uniform with a first surface 38 that faces in the anterior direction 23 being substantially the same as a second surface 37 that faces in a posterior direction.

Figure 8:
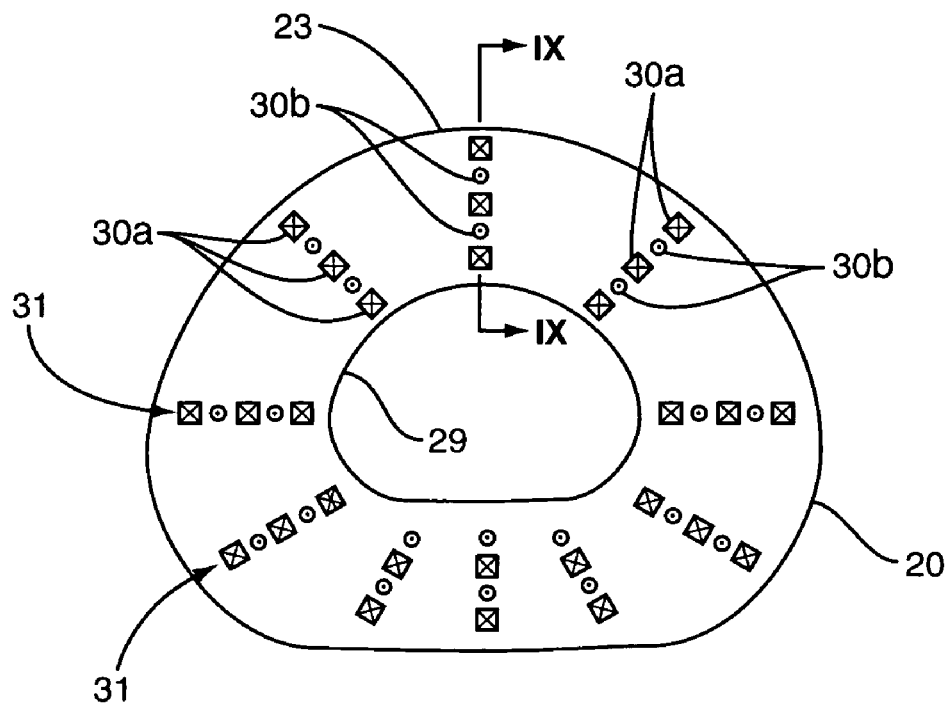
FIG. 8 is a top view illustrating an implant according to one embodiment.
Figure 9:
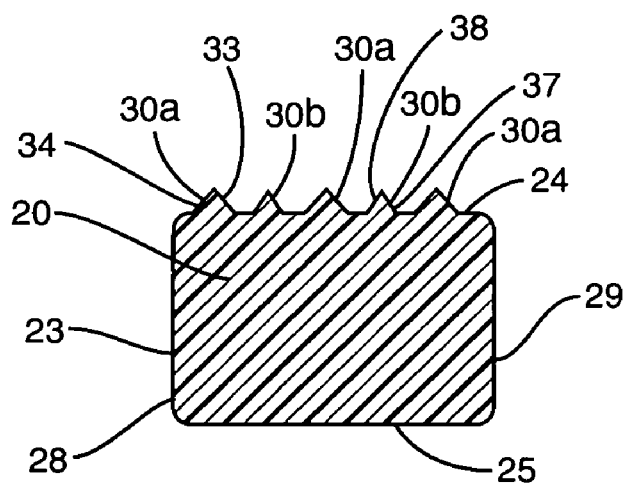
FIG. 9 is a cross-section view cut along line IX-IX of FIG. 8 illustrating an implant according to one embodiment.

Different shaped teeth 30 may also be positioned on a single surface. FIG. 8 illustrates an embodiment with each row 31 including a first tooth 30a and a second tooth 30b. Teeth 30a, 30b include different shapes and may perform different functions. By way of example, teeth 30a may be oriented to resist expulsion of the implant 10 in a variety of directions. Teeth 30b may function to bite into the vertebral members once the implant is positioned.

The implant 10 may be used in a variety of different vertebral applications. Implant 10 may be inserted within the cervical, thoracic, lumbar, and sacrococcygeal regions. Further, the implant may be constructed to access the intervertebral space from various approach angles to the spine, including an anterior, posterior, postero-lateral, antero-lateral and lateral.

Terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. In one embodiment, opening 21 is positioned within the body 20 at a point that is off-center. The present embodiments are, therefore, to be considered in all respects as illustrative and not restrictive, and all changes coming within the meaning and equivalency range of the appended claims are intended to be embraced therein.

What is claimed is:

1. An intervertebral implant comprising:
   a body including inferior and superior surfaces and an opening;
   a plurality of teeth positioned across at least one of the inferior and superior surfaces, the plurality of teeth being arranged in radial rows aligned from a central point of the body and extending outward towards an outer edge of the body, each of the rows being spaced apart forming aisles therebetween;
   each of the plurality of teeth including a first surface extending upward from the at least one of the inferior and superior surfaces at a first angle and a second surface extending upward from the at least one of the inferior and superior surfaces at a second angle greater than the first angle, each of the first surfaces facing towards the central point and each of the second surfaces facing away from the central point.

2. The implant of claim 1, wherein the opening is positioned at a center of the body.

3. The implant of claim 1, wherein the body further comprises a tapered section positioned along the outer edge, the tapered section includes a first height at the outer edge that increases to a second height at an interior section of the body.

4. The implant of claim 1, wherein a width of the teeth increases from an inner edge at the opening to the outer edge.

5. The implant of claim 4, wherein an aisle width is substantially constant from the inner edge to the outer edge.

6. The implant of claim 1, wherein each of the plurality of teeth includes a first ramped surface that angles towards the outer edge and a second surface that is substantially parallel to the outer edge.

7. The implant of claim 1, wherein the plurality of teeth include a first type with a first shape and a second type with a second different shape.

8. The implant of claim 7, wherein at least one of the rows of teeth include the first type and the second type.

9. An intervertebral implant comprising:
a body including inferior and superior surfaces and an outer edge, the body further comprising a first section with a substantially constant first height and a second tapered section positioned along a portion of the outer edge, the tapered section increasing from a second height at the outer edge to the first height towards an interior of the body; and
rows of teeth positioned across at least one of the inferior and superior surfaces, the rows being aligned with a central point of the body and extending outward towards the outer edge of the body, each of the rows being spaced apart forming aisles therebetween;
each of the plurality of teeth including a first surface extending upward from the at least one of the inferior and superior surfaces at a first angle and a second surface extending upward from the at least one of the inferior and superior surfaces at a second angle greater than the first angle, the first surface facing toward the central point and the second surface facing away from the central point.

10. The implant of claim 9, wherein the rows of teeth are spaced away from the second tapered section.

11. The implant of claim 9, wherein the rows of teeth are positioned on the inferior and superior surfaces.

12. The implant of claim 9, wherein each of the teeth include a first ramped surface that angles towards the outer edge and a second surface that is substantially parallel to the outer edge.

13. The implant of claim 9, wherein the rows of teeth include a first type with a first shape and a second type with a second different shape.

14. The implant of claim 9, wherein the inferior and superior surfaces are each tapered.

15. The implant of claim 9, wherein the inferior surface is substantially flat and the superior surface is tapered.

16. The implant of claim 9, wherein the inferior and superior surfaces of the first section are parallel.

17. The implant of claim 9, wherein the inferior and superior surfaces of the first section are non-parallel.

18. An intervertebral implant comprising:
a body including inferior and superior surfaces and an outer edge, the body further comprising a first section and a second tapered section positioned along a section of the outer edge;
an opening positioned within a central section of the body and forming an inner edge; and
rows of teeth positioned across at least one of the inferior and superior surfaces, the rows being aligned with a point within the opening and extending from the inner edge to the outer edge of the body, each of the rows being spaced apart forming aisles therebetween, and a width of the aisles increases from the inner edge to the outer edge.

19. The implant of claim 18, wherein a width of the teeth increases from the inner edge to the outer edge.

20. The implant of claim 19, wherein an aisle width formed between the rows of teeth is substantially constant from the inner edge to the outer edge.

21. The implant of claim 18, wherein each of the teeth includes a first ramped surface that angles towards the outer edge and a second surface that is substantially parallel to the outer edge.

22. The implant of claim 18, wherein the rows of teeth include a first type with a first shape and a second type with a second different shape.

23. The implant of claim 18, wherein the rows of teeth are spaced away from the second tapered section.

24. The implant of claim 18, wherein each of the inferior and superior surfaces are tapered.

25. The implant of claim 18, wherein the inferior surface is substantially flat and the superior surface is tapered.

26. The implant of claim 18, wherein a height of the tapered section increases from a minimum at the outer edge to a maximum at an interior of the body.

* * * * *